United States Patent
Zhang et al.

(10) Patent No.: US 9,187,508 B2
(45) Date of Patent: Nov. 17, 2015

(54) CRYSTALLINE FORMS OF TENOFOVIR DIPIVOXIL FUMARATE

(75) Inventors: Aiming Zhang, Jiangsu (CN); Qide Li, Jiangsu (CN); Chunguang Xia, Jiangsu (CN); Xiquan Zhang, Jiangsu (CN)

(73) Assignee: Jiangsu Chiatai Tianqing Pharmaceutical Co., LTD., Jiangsu (CN)

(*) Notice: Subject to any disclaimer, the term of this patent is extended or adjusted under 35 U.S.C. 154(b) by 123 days.

(21) Appl. No.: 13/813,644

(22) PCT Filed: Aug. 1, 2011

(86) PCT No.: PCT/CN2011/077871
§ 371 (c)(1),
(2), (4) Date: Aug. 12, 2013

(87) PCT Pub. No.: WO2012/016506
PCT Pub. Date: Feb. 9, 2012

(65) Prior Publication Data
US 2013/0324498 A1 Dec. 5, 2013

(30) Foreign Application Priority Data
Aug. 1, 2010 (CN) .......................... 2010 1 0245715

(51) Int. Cl.
*A61K 31/675* (2006.01)
*C07C 57/15* (2006.01)
*C07F 9/6561* (2006.01)

(52) U.S. Cl.
CPC ............. *C07F 9/65616* (2013.01); *C07C 57/15* (2013.01)

(58) Field of Classification Search
CPC . C07F 9/6561; C07F 9/65616; A61K 31/675; C07C 57/15
USPC ............................................ 544/244; 514/81
See application file for complete search history.

(56) References Cited

U.S. PATENT DOCUMENTS
2010/0216822 A1  8/2010  Yuan

FOREIGN PATENT DOCUMENTS
CN  1986553 A  6/2007

OTHER PUBLICATIONS

WebMD. Bacterial and Viral Infections. 2013 < http://www.webmd.com/a-to-z-guides/bacterial-and-viral-infections?page=2>.*
Benhamou, Yves. Heptology vol. 43, No. 3 (2006) 548-554.*
Clercq, Erik. Journal of Clinical Virology 30 (2004) 115-133.*
MayoClinic. HIV/AIDS: Prevention. (2015) < http://www.mayoclinic.org/diseases-conditions/hiv-aids/basics/prevention/con-20013732>.*
NIH. AIDSInfo. Tenofovir Disproxil Fumarate. (2014) < http://aidsinfo.nih.gov/drugs/290/tenofovir-disoproxil-fumarate/0/patient>.*
Pharmacopoeia Commission, "Guidelines for the Stability Testing of Drug Substances and preparations," in *Pharmacopoeia of the People's Republic of China 2010*, vol. II, Chapter XIX C, pp. 199-201 (2010).
International Search Report dated Nov. 10, 2011, issued in related International Patent Application No. PCT/CN2011/077871, filed Aug. 1, 2011.

* cited by examiner

*Primary Examiner* — Golam M M Shameem
*Assistant Examiner* — Laura Daniel
(74) *Attorney, Agent, or Firm* — Kilpatrick Townsend & Stockton LLP (57) ABSTRACT

The present invention relates to a crystalline form of tenofovir dipivoxil fumarate, a crystalline composition and a pharmaceutical composition comprising the crystalline form, and also to a process for preparing the same and the use for prophylaxis or treatment of a disease associated with a viral infection. The crystalline form has an X-ray powder diffraction pattern using Cu-Kα radiation, expressed in terms of lattice spacing "d" comprising peaks at about 18.4714 Å, 5.0350 Å, 4.6380 Å, 4.5347 Å, 4.3838 Å, 4.2874 Å and 3.6304 Å.

17 Claims, 8 Drawing Sheets

Fig. 1

| Peak no. | 2theta | Flex Width | d-value | Intensity | I/Io | Peak no. | 2theta | Flex Width | d-value | Intensity | I/Io |
|---|---|---|---|---|---|---|---|---|---|---|---|
| 1 | 4.780 | 0.212 | 18.4714 | 6197 | 56 | 16 | 19.120 | 0.212 | 4.6380 | 6930 | 62 |
| 2 | 6.820 | 0.235 | 12.9501 | 1322 | 12 | 17 | 19.560 | 0.329 | 4.5347 | 8055 | 72 |
| 3 | 8.780 | 0.235 | 10.0631 | 1065 | 10 | 18 | 20.240 | 0.329 | 4.3838 | 6857 | 62 |
| 4 | 9.400 | 0.212 | 9.4007 | 1760 | 16 | 19 | 20.700 | 0.235 | 4.2874 | 8532 | 76 |
| 5 | 10.060 | 0.212 | 8.7854 | 3228 | 29 | 20 | 21.780 | 0.235 | 4.0772 | 3399 | 31 |
| 6 | 10.620 | 0.212 | 8.3234 | 4686 | 42 | 21 | 22.540 | 0.282 | 3.9414 | 5184 | 47 |
| 7 | 12.120 | 0.259 | 7.2964 | 2059 | 19 | 22 | 23.160 | 0.235 | 3.8373 | 2027 | 19 |
| 8 | 13.160 | 0.235 | 6.7220 | 4256 | 38 | 23 | 24.500 | 0.259 | 3.6304 | 8900 | 80 |
| 9 | 13.740 | 0.424 | 6.4396 | 4374 | 39 | 24 | 25.020 | 0.259 | 3.5561 | 3346 | 30 |
| 10 | 14.540 | 0.259 | 6.0870 | 4480 | 40 | 25 | 26.600 | 0.235 | 3.3483 | 1834 | 17 |
| 11 | 15.460 | 0.282 | 5.7268 | 3690 | 33 | 26 | 27.620 | 0.353 | 3.2269 | 1710 | 16 |
| 12 | 16.680 | 0.259 | 5.3106 | 2442 | 22 | 27 | 28.560 | 0.353 | 3.1228 | 2131 | 19 |
| 13 | 17.600 | 0.282 | 5.0350 | 11240 | 100 | 28 | 29.560 | 0.165 | 3.0194 | 2550 | 23 |
| 14 | 18.180 | 0.282 | 4.8756 | 3785 | 34 | 29 | 29.960 | 0.306 | 2.9800 | 3347 | 30 |
| 15 | 18.760 | 0.235 | 4.7262 | 5493 | 49 | 30 | 34.480 | 0.400 | 2.5990 | 1798 | 16 |

| Peak no. | 2theta | Flex Width | d-value | Intensity | I/Io | Peak no. | 2theta | Flex Width | d-value | Intensity | I/Io |
|---|---|---|---|---|---|---|---|---|---|---|---|
| 1 | 4.800 | 0.212 | 18.3945 | 24766 | 66 | 16 | 21.560 | 0.282 | 4.1183 | 5429 | 15 |
| 2 | 10.080 | 0.165 | 8.7680 | 1817 | 5 | 17 | 22.060 | 0.212 | 4.0261 | 2667 | 8 |
| 3 | 10.320 | 0.188 | 8.5646 | 2442 | 7 | 18 | 22.560 | 0.259 | 3.9380 | 2775 | 8 |
| 4 | 10.680 | 0.306 | 8.2767 | 2333 | 7 | 19 | 23.140 | 0.259 | 3.8406 | 2359 | 7 |
| 5 | 13.080 | 0.306 | 6.7630 | 2564 | 7 | 20 | 23.600 | 0.235 | 3.7667 | 2732 | 8 |
| 6 | 13.640 | 0.259 | 6.4865 | 3036 | 9 | 21 | 24.500 | 0.306 | 3.6304 | 37803 | 100 |
| 7 | 14.580 | 0.235 | 6.0704 | 15484 | 41 | 22 | 25.020 | 0.235 | 3.5561 | 3698 | 10 |
| 8 | 14.920 | 0.141 | 5.9328 | 2468 | 7 | 23 | 26.600 | 0.188 | 3.3483 | 2204 | 6 |
| 9 | 15.420 | 0.212 | 5.7415 | 2860 | 8 | 24 | 27.460 | 0.329 | 3.2454 | 2775 | 8 |
| 10 | 15.780 | 0.212 | 5.6114 | 2841 | 8 | 25 | 28.840 | 0.353 | 3.0932 | 2463 | 7 |
| 11 | 17.500 | 0.329 | 5.0635 | 9062 | 24 | 26 | 29.540 | 0.306 | 3.0214 | 14826 | 40 |
| 12 | 18.400 | 0.259 | 4.8178 | 3161 | 9 | 27 | 29.960 | 0.235 | 2.9800 | 3539 | 10 |
| 13 | 19.540 | 0.235 | 4.5392 | 25698 | 68 | 28 | 34.620 | 0.259 | 2.5888 | 4099 | 11 |
| 14 | 20.120 | 0.212 | 4.4097 | 3460 | 10 | | | | | | |
| 15 | 20.760 | 0.376 | 4.2752 | 3875 | 11 | | | | | | |

CRYSTALLINE FORMS OF TENOFOVIR DIPIVOXIL FUMARATE

FIELD OF THE INVENTION

The present application is a U.S. National Phase of PCT/CN2011/077871, filed Aug. 1, 2011, which claims benefit of Chinese Patent Application No. 201010245715.5, filed Aug. 1, 2010, each of which are incorporated by reference for all purposes.

BACKGROUND OF THE INVENTION

Phosphonomethoxy nucleotide analogs are a class of known broad-spectrum anti-viral compounds with activities against HIV, HBV, CMV, HSV-1, HSV-2, human herpes virus as well as other viruses. 9-[2-(phosphonomethoxy)ethyl]adenine (PMEA) and 9-[(R)-2-(phosphonomethoxy)propyl]adenine (PMPA) are two examples of this kind of compounds that have been used in the clinical anti-viral treatment. Because of the influence of a phosphonic acid group in a phosphonomethoxy nucleotide analog on its absorption in human body, a phosphonomethoxy nucleotide analog usually needs to be converted to its lipophilic prodrug to enhance bioavailability. Tenofovir disoproxil approved by FDA to treat AIDS is a lipophilic prodrug of PMPA, which can be metabolized in vivo to its corresponding parent drug PMPA with anti-viral activity.

PCT patent application WO 2006/133632 discloses crystalline forms, salts, amorphous solid forms and the like of tenofovir dipivoxil represented by Formula II. It also discloses tenofovir dipivoxil fumarate represented by Formula I and a crystalline form thereof (hereinafter referred to as crystalline form A).

Formula II

Formula I

SUMMARY OF THE INVENTION

In one aspect, the present invention provides crystalline form B of tenofovir dipivoxil fumarate represented by Formula I.

Formula I

In another aspect, the present invention provides a crystalline composition of crystalline form B, wherein the crystalline form B is more than 50% by weight of the crystalline composition, preferably more than 80%, more preferably more than 90%, and most preferably more than 95%.

In another aspect, the present invention provides a pharmaceutical composition comprising a therapeutically effective amount of the crystalline form B or the crystalline composition of crystalline form B.

In another aspect, the present invention provides a method for prophylaxis or treatment of a viral infection in a mammal, comprising administrating a therapeutically effective amount of the crystalline form B, the crystalline composition of crystalline form B, or the pharmaceutical composition to the mammal in need thereof.

In another aspect, the present invention provides use of the crystalline form B, the crystalline composition of crystalline form B, or the pharmaceutical composition for manufacture of a medicament for prophylaxis or treatment of a disease associated with a viral infection.

In another aspect, the present invention provides a process for preparing the crystalline form B or the crystalline composition of crystalline form B, comprising
(a) dissolving tenofovir dipivoxil fumarate in an organic solvent by heating, wherein the organic solvent is a lower alcohol or a lower ketone;
(b) adding water; and
(c) precipitating a crystalline form of tenofovir dipivoxil fumarate.

DETAILED DESCRIPTION OF THE INVENTION

Definition

Unless specifically defined otherwise, the following terms used in the specification and claims appended hereto have the following meanings.

"Mammals" include humans, domestic animals such as laboratory mammals and house pets (for example cats, dogs, pigs, cattle, sheep, goats, horses and rabbits), and non-domestic mammals such as wild mammals and the like.

The term "pharmaceutical composition" refers to a formulation comprising the compound of the present invention and media usually acceptable in the art for delivering a biologically active compound to a mammal (such as human). The media include all suitable pharmaceutically acceptable carriers. A pharmceutical composition facilitates administration of a compound to an organism.

The term "carrier" is defined as a compound beneficial to deliver a compound into cells or tissues. For example, dimethylsulfoxide (DMSO) is usually used as a carrier, as it can easily deliver some organic compounds into cells or tissues of an organism.

"Pharmaceutically acceptable carrier" includes but not limited to any adjuvants, excipients, glidants, sweeteners, diluents, preservatives, dyes/colorants, flavoring agents, surfactants, wetting agents, dispersing agents, suspending agents, stabilizing agents, isotonic agents, solvents or emulsors, which are approved by the State Drug Administration for use in humans or domestic animals.

"Therapeutically effective amount" refers to an amount of a compound of the present invention that, when administered to a mammal, preferably human, is sufficient to achieve the treatment of a viral infection in a mammal, preferably in a human, as defined hereinafter. A "therapeutically effective amount" of a compound of the present invention will vary depending on the compound, the disease or condition and its severity, the route of administration and the age of the mammal to be treated.

However, it can be routinely determined by those ordinary skilled in the art according to their knowledge and the disclosure of the present invention.

"Treatment" used herein includes any therapeutic treatment of a viral infection in a mammal, preferably in human, which comprises
(i) inhibiting a viral infection, i.e., preventing its development;
(ii) ameliorating a viral infection, i.e., leading to recovering from a viral infection; or
(iii) relieving symptoms caused by a viral infection.

Embodiments of the Invention

In one aspect, the present invention provides crystalline form B of tenofovir dipivoxil fumarate represented by Formula I.

Formula I

Crystalline form B of tenofovir dipivoxil fumarate of the present invention has an XRD pattern using Cu-Kα radiation, expressed in terms of lattice spacing "d" comprising peaks at about 18.4714 Å, 5.0350 Å, 4.6380 Å, 4.5347 Å, 4.3838 Å, 4.2874 Å, and 3.6304 Å, typically comprising peaks at about 18.4714 Å, 8.3234 Å, 6.0870 Å, 5.0350 Å, 4.7262 Å, 4.6380 Å, 4.5347 Å, 4.3838 Å, 4.2874 Å, 3.9414 Å and 3.6304 Å, more typically comprising peaks at about 18.4714 Å, 8.3234 Å, 6.7220 Å, 6.4396 Å, 6.0870 Å, 5.0350 Å, 4.7262 Å, 4.6380 Å, 4.5347 Å, 4.3838 Å, 4.2874 Å, 3.9414 Å and 3.6304 Å, and further more typically comprising peaks at about 18.4714 Å, 8.7854 Å, 8.3234 Å, 6.7220 Å, 6.4396 Å, 6.0870 Å, 5.7268 Å, 5.3106 Å, 5.0350 Å, 4.8756 Å, 4.7262 Å, 4.6380 Å, 4.5347 Å, 4.3838 Å, 4.2874 Å, 4.0772 Å, 3.9414 Å, 3.6304 Å, 3.5561 Å, 3.0194 Å and 2.9800 Å.

Crystalline form B of tenofovir dipivoxil fumarate of the present invention has a DSC with the onset temperature of endothermic transition temperature of 120° C. and the peak temperature of about 121° C. under the heating rate of 10° C./min.

Crystalline form B of tenofovir dipivoxil fumarate of the present invention has an IR spectrum with the absorption peaks at 3208 $cm^{-1}$, 1748 $cm^{-1}$ and 1689 $cm^{-1}$.

Figure 1:
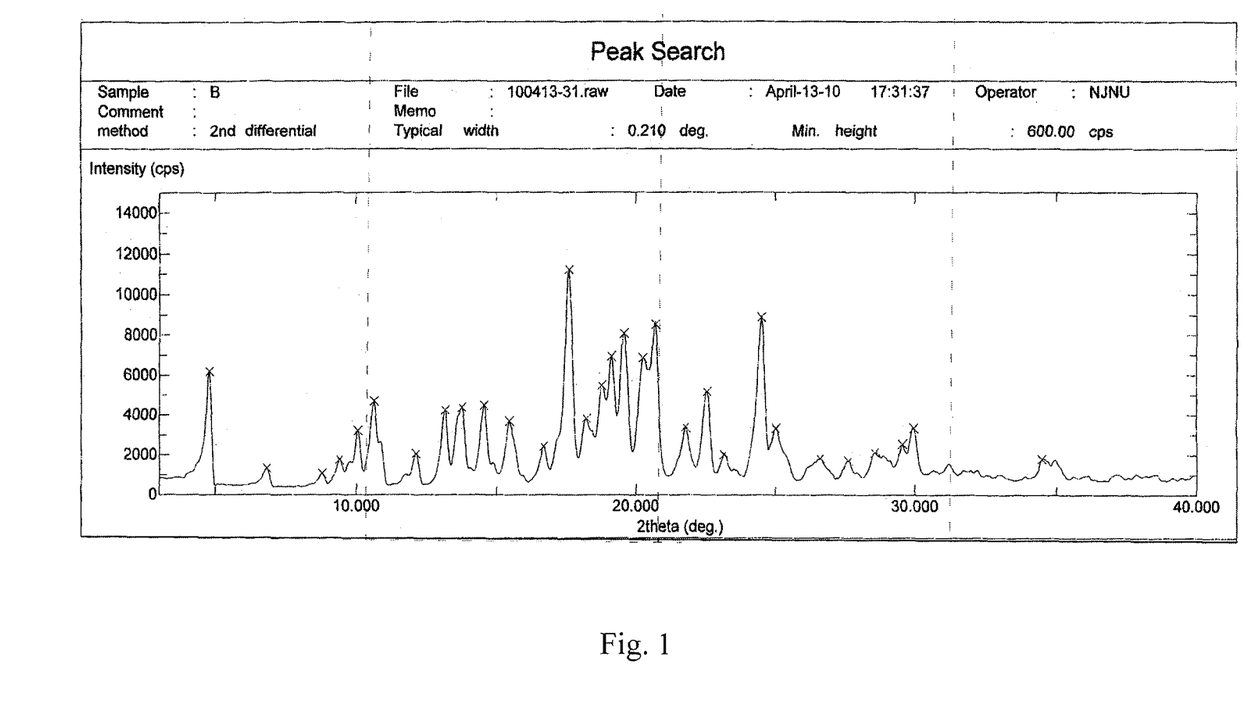
FIG. 1 shows XRD (X-ray Powder Diffraction) pattern of crystalline form B of tenofovir dipivoxil fumarate in Example 1.

A typical but non-limited embodiment of crystalline form B of tenofovir dipivoxil fumarate of the present invention has an XRD pattern as shown in FIG. 1, which has the following features:

| No. | 2θ | d-value/Å | I/I$_0$ |
|---|---|---|---|
| 1 | 4.78 | 18.4714 | 56 |
| 2 | 6.82 | 12.9501 | 12 |
| 3 | 8.78 | 10.0631 | 10 |
| 4 | 9.40 | 9.4007 | 16 |
| 5 | 10.06 | 8.7854 | 29 |
| 6 | 10.62 | 8.3234 | 42 |
| 7 | 12.12 | 7.2964 | 19 |
| 8 | 13.16 | 6.7220 | 38 |
| 9 | 13.74 | 6.4396 | 39 |
| 10 | 14.54 | 6.0870 | 40 |
| 11 | 15.46 | 5.7268 | 33 |
| 12 | 16.68 | 5.3106 | 22 |
| 13 | 17.60 | 5.0350 | 100 |
| 14 | 18.18 | 4.8756 | 34 |
| 15 | 18.76 | 4.7262 | 49 |
| 16 | 19.12 | 4.6380 | 62 |
| 17 | 19.56 | 4.5347 | 72 |
| 18 | 20.24 | 4.3838 | 62 |
| 19 | 20.70 | 4.2874 | 76 |
| 20 | 21.78 | 4.0772 | 31 |
| 21 | 22.54 | 3.9414 | 47 |
| 22 | 23.16 | 3.8373 | 19 |
| 23 | 24.50 | 3.6304 | 80 |
| 24 | 25.02 | 3.5561 | 30 |
| 25 | 26.60 | 3.3483 | 17 |
| 26 | 27.62 | 3.2269 | 16 |
| 27 | 28.56 | 3.1228 | 19 |
| 28 | 29.56 | 3.0194 | 23 |
| 29 | 29.96 | 2.9800 | 30 |
| 30 | 34.48 | 2.5990 | 16 |

Figure 2:
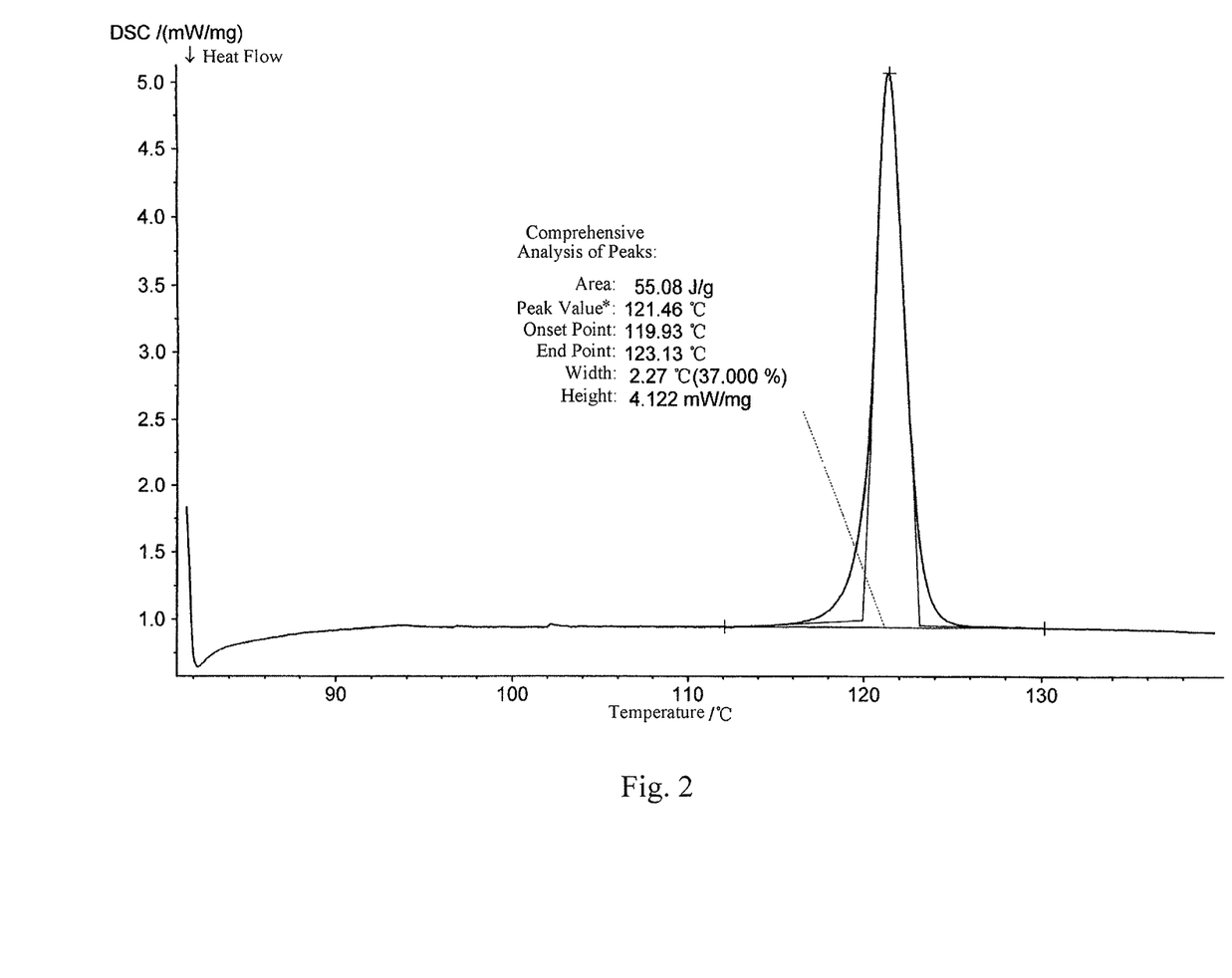
FIG. 2 shows DSC (Differential Scanning calorimetry) thermogram of crystalline form B of tenofovir dipivoxil fumarate in Example 1.

A typical but non-limited embodiment of crystalline form B of tenofovir dipivoxil fumarate of the present invention has an DSC thermogram as shown in FIG. 2 under the heating rate of 10° C./min.

Figure 3:
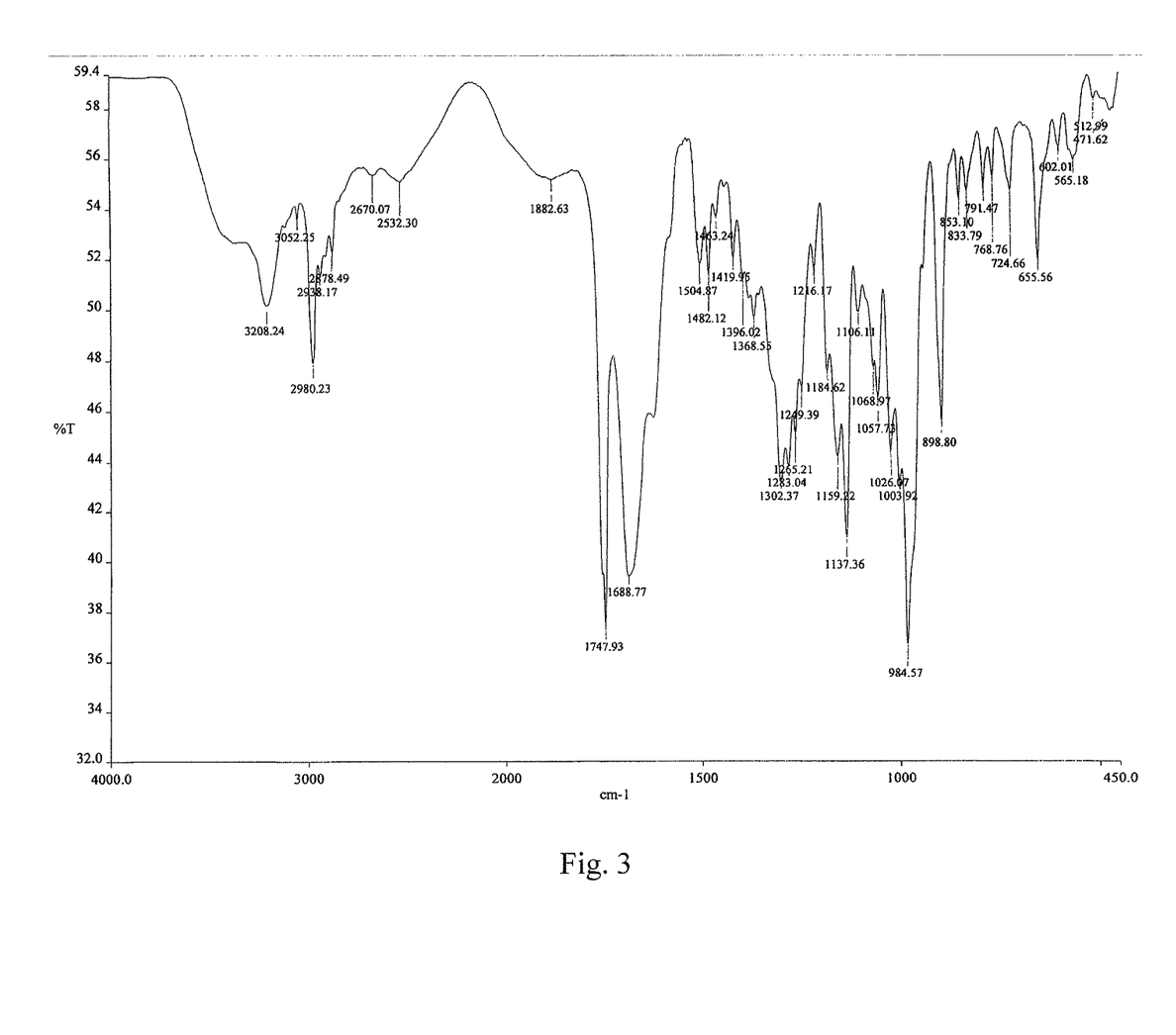
FIG. 3 shows IR (Infrared Absorption Spectroscopy) spectrum of crystalline form B of tenofovir dipivoxil fumarate in Example 1.

A typical but non-limited embodiment of crystalline form B of tenofovir dipivoxil fumarate of the present invention has an IR spectrum as shown in FIG. 3.

Crystalline form B of tenofovir dipivoxil fumarate of the present invention has an excellent stability and low residual solvent content, and can be easily prepared. In addition, crystalline form B of tenofovir dipivoxil fumarate of the present invention exhibits an excellent flowability and therefore is suitable for preparing a pharmaceutical formulation.

It should be noticed that in XRD, a diffraction pattern of a crystalline compound is characteristic for a specific crystalline form. Relative intensities of the bands (especially at the low angle) can vary depending upon the crystallization conditions, particle size, preferential orientation effects resulting from the difference of other measuring conditions. Therefore, relative intensities of diffraction peaks are not characteristic for a specific crystalline form. It is the relative position of peaks rather than relative intensities that should be paid more attention when judging whether a crystalline form is the same as the known crystalline form. Usually, the position of a peak is expressed in terms of 2θ angle or lattice spacing d in XRD. As 2θ angle is related to the wavelength of incident X-ray, lattice spacing d is more representative. The simple conversion relationship between them is d=λ/2 sin θ, wherein d represents the lattice spacing, represents the wavelength of incident X-ray, and θ represents the diffraction angle. For the same crystalline form of the same compound, the XRD patterns thereof have similarities on the whole. In general, the error of d representing the position of a peak is about ±2%, most of the error is no more than ±1%; the error of relative intensities can be relatively large, but the trends are the same. Furthermore, an XRD pattern must be considered as a whole while judging whether a crystalline form is the same as the known crystalline form, as it is a set of specific "d-I/I1" data that represents a certain phase rather than a single diffraction line. In addition, due to some factors such as reduced contents, parts of diffraction lines will be absent in identification of a mixture. At this time, even a band may be characteristic for the given crystalline form without depending upon the whole bands of a high purity sample.

DSC is used to measure the thermal transition temperature when absorbing or releasing heat due to crystalline form structure change or crystal melting. In a continuous analysis of the same crystalline form of the same compound, the error between thermal transition temperature and melting point is typically within a range of about ±5° C., generally within a range of about ±3° C. A compound with a given DSC peak or melting point means that DSC peak or melting point may be varied within a range of ±5° C. DSC provides an auxiliary method to distinguish different crystalline forms. Different crystalline forms can be identified by their characteristically different transition temperatures. It is necessary to point out that DSC peak or melting point of a mixture will vary over a wider range. Furthermore, because of the decomposition in the melting process, the melting temperature is closely related to heating rates.

IR is used to measure infrared absorption caused by specific chemical bonds relating to vibrating groups initiated by light in a molecule. The different electronic environment of covalent bonds in molecules of different crystalline forms results in the variation of intensities of covalent bonds which inevitably results in that different crystalline forms have different IR spectrums.

In another aspect, the present invention provides a crystalline composition of crystalline form B of tenofovir dipivoxil fumarate, wherein the crystalline form B is more than 50% by weight of the crystalline composition, preferably more than 80%, more preferably more than 90%, and most preferably more than 95%. In addition to the crystalline form B, the crystalline composition may further comprise a small amount of other crystalline forms and amorphous forms of tenofovir dipivoxil fumarate.

In another aspect, the present invention provides a process for preparing crystalline form B of tenofovir dipivoxil fumarate or a crystalline composition of crystalline form B, comprising
 (a) dissolving tenofovir dipivoxil fumarate in an organic solvent by heating, wherein the organic solvent is a lower alcohol or a lower ketone;
 (b) adding water; and
 (c) precipitating a crystalline form of tenofovir dipivoxil fumarate.

In some preferable embodiments, the step (c) is carried out under cooling.

In some preferable embodiments, the process for preparing crystalline form B or a crystalline composition thereof further comprises
 (d) filtrating; and
 (e) drying.

A more preferable process comprises
 (a) dissolving tenofovir dipivoxil fumarate in an organic solvent by heating, wherein 2 Kg to 6 Kg of the organic solvent is added per kilogram of tenofovir dipivoxil fumarate, the organic solvent is selected from one or more solvents of methanol, ethanol, propanol, isopropanol, n-butanol, isobutanol, tert-butanol, acetone and butanone, and the heating temperature range is 35° C. to 70° C.;
 (b) adding water, wherein 5 Kg to 15 Kg of water is added per kilogram of tenofovir dipivoxil fumarate; and (c) precipitating a crystalline form of tenofovir dipivoxil fumarate.

In some more preferable embodiments, the step (c) is carried out with cooling to a temperature of −10° C. to 5° C.

In some more preferable embodiments, the process for preparing crystalline form B of tenofovir dipivoxil fumarate or a crystalline composition thereof further comprises (d) filtrating; and (e) drying under reduced pressure at 40° C. to 70° C.

In the present invention, a lower alcohol refers to an alcohol having 1 to 6 carbon atoms, including but not limited to methanol, ethanol, propanol, isopropanol, n-butanol, isobutanol, tert-butanol, pentan-1-ol, pentan-2-ol, pentan-3-ol, 2-methylbutan-1-ol, 3-methylbutan-1-ol, 2-methylbutan-2-ol, 3-methylbutan-2-ol, 2,2-dimethylpropan-1-ol, and hexan-1-ol, preferably an alcohol having 1 to 4 carbon atoms.

In the present invention, a lower ketone refers to a ketone having 3 to 6 carbon atoms, including but not limited to acetone, butanone, pentan-2-one, pentan-3-one, hexan-2-one, and hexan-3-one, preferably acetone and butanone.

In another aspect, the present invention provides a pharmaceutical composition comprising a therapeutically effective amount of crystalline form B of tenofovir dipivoxil fumarate represented by Formula I or a crystalline composition thereof and other pharmaceutically acceptable excipients. If needed, the pharmaceutical composition may further comprise other therapeutic ingredients or auxiliary ingredients, such as other antiviral agents, immunostimulants, liver protective agents, L-carnitine and salts thereof, and the like. Pharmaceutically acceptable excipients include but not limited to any one or more of adhesive agents, diluents, disintegrating agents, preservatives, dispersing agents, glidants (anti-tack agents) and lubricants.

Usually, a pharmaceutical composition of the present invention may be administered orally, rectally, vaginally, intranasally, locally(including intraoccularly, intraorally and sublingually) or parenterally (including subcutaneously, intramuscularly, intravenously, intradermally, intrathecally and epidurally), etc. Oral administration is preferable.

The preferable dosage form of a pharmaceutical composition of the present invention is a tablet, capsule, powder, granule, dropping pill, pulvis, bolus, tincture or cataplasm. A preferable tablet is a conventional tablet, dispersible tablet, effervescent tablet, sustained-release tablet, controlled-release tablet or enteric-coated tablet. A preferable capsule is a conventional capsule, sustained-release capsule, controlled-release capsule or enteric-coated capsule.

When the pharmaceutical composition provided herein is a tablet or capsule, the amount of the crystalline form B or a crystalline composition thereof as an active ingredient in a unit dosage form may vary depending upon many factors such as the symptom or age. Usually, a one-time amount of an active ingredient administrated orally is 5 mg to 300 mg, preferably 5 mg to 150 mg. In addition, the tablet or capsule may further comprise an appropriate amount of bulking agent such as starch, sucrose, lactose and the like; adhesive agent such as water, alcohol, polyvinylpyrrolidone, pregelatinized starch and the like; disintegrating agent such as microcrystalline cellulose, croscarmellose sodium, crosslinked polyvinylpyrrolidone and the like; lubricant such as magnesium stearate, talcum powder, silica and the like. Further, formaldehyde scavenger (such as lysine or gelatin) may be also added to catch formaldehyde released during storage of crystalline form B.

When the pharmaceutical composition provided herein is a tablet or capsule, it preferably comprises a basic pharmaceutical carrier including a basic carbonate and a basic hydroxide. A preferable basic carbonate is calcium carbonate, magnesium carbonate, zinc carbonate, ferrous carbonate or aluminium carbonate. A preferable basic hydroxide is magnesium hydroxide, calcium hydroxide, aluminium hydroxide or ferrous hydroxide. The basic pharmaceutical carriers can improve stability and reduce degradation of the crystalline form B in a formulation.

When the pharmaceutical composition provided herein is a tablet or capsule, it preferably comprises L-carnitine or a salt thereof (such as L-carnitine-L-tartrate (2:1)). Pivalic acid produced by metabolism of tenofovir dipivoxil fumarate in vivo may reduce the level of L-carnitine in a patient. A pharmaceutical composition comprising L-carnitine or a salt thereof may decrease the effects of pivalic acid on L-carnitine depletion in a patient taking tenofovir dipivoxil fumarate.

When a pharmaceutical composition is a dispersing tablet, a disintegrating agent is optionally present at a level about 0.5%-60% so as to disintegrate rapidly.

The dosage form of a pharmaceutical composition of the present invention can also be a sterile powder for injection and an injection solution, wherein the dosage form can be administrated by injection.

In another aspect, the present invention provides a method for prophylaxis or treatment of a viral infection in a mammal, comprising administrating a therapeutically effective amount of crystalline form B, a crystalline composition thereof, or a pharmaceutical composition thereof to a mammal in need thereof.

In another aspect, the present invention provides use of crystalline form B, a crystalline composition of crystalline form B, or a pharmaceutical composition aforementioned for manufacture of a medicament for prophylaxis or treatment of a disease associated with a viral infection.

The virus herein includes HIV, HBV, CMV, HSV-1, HSV-2 and human herpes virus, preferably HIV or HBV.

The crystalline form, crystalline composition and pharmaceutical composition of the present invention are preferably suitable for a warm-blooded animal, more preferably human.

The following examples further illustrate the invention but do not limit the scope thereof.

COMPARATIVE EXAMPLE 1

Preparation of Crystalline Form A of Tenofovir Dipivoxil Fumarate

To 4 kg of methanol was added 1 kg of tenofovir dipivoxil fumarate. The resulting mixture was heated to 50° C. and stirred. After tenofovir dipivoxil fumarate was dissolved, 8 kg of diisopropyl ether was added. The mixture was stirred and cooled to 5° C., stood for crystallization for 4 h, and then filtered and dried under reduced pressure at 60° C. to give 0.7 kg of crystalline form A of tenofovir dipivoxil fumarate.

The preparation of tenofovir dipivoxil fumarate was carried out according to Example 24 of WO 2006/133632.

Figure 4:
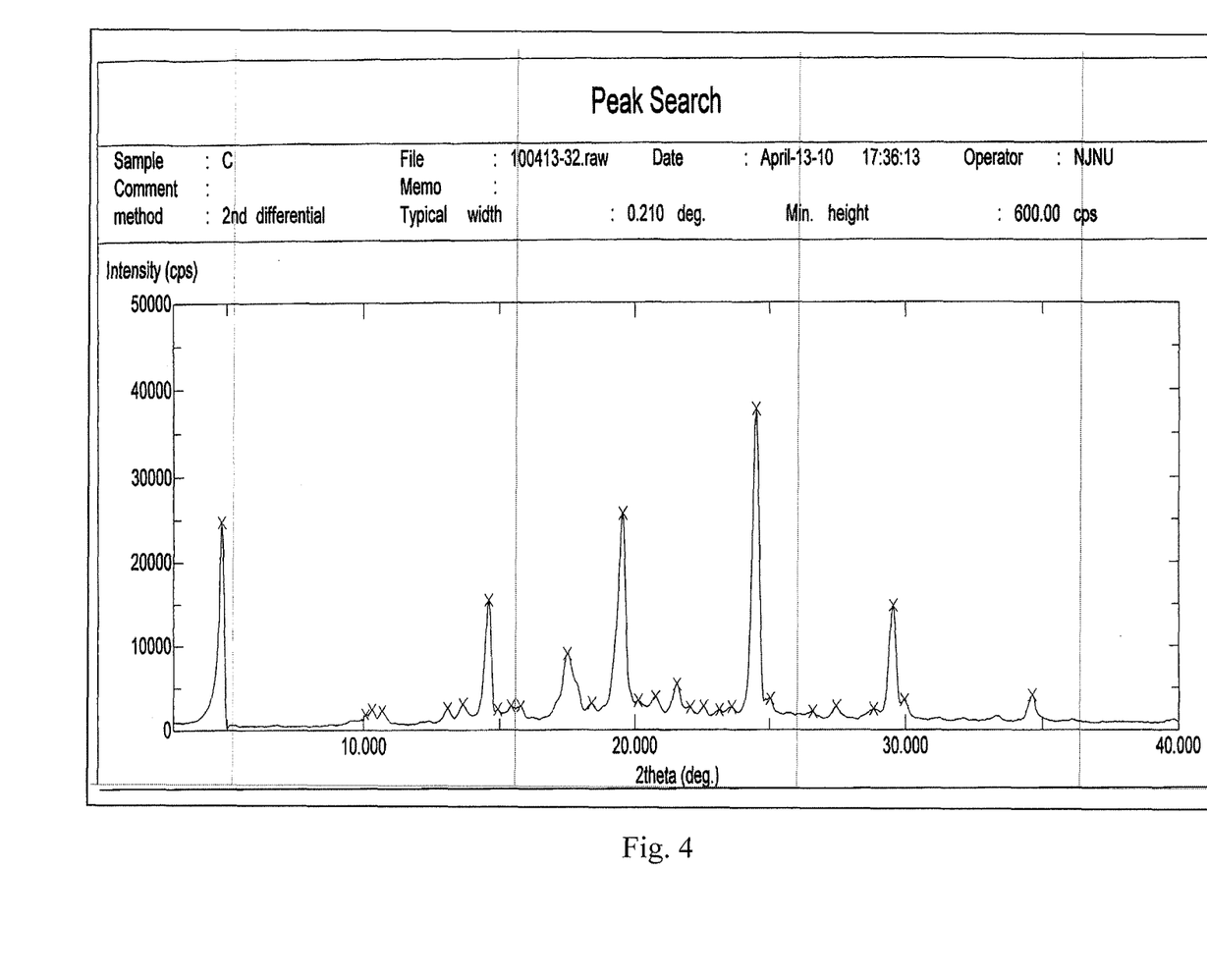
FIG. 4 shows XRD pattern of crystalline form A of tenofovir dipivoxil fumarate in Comparative Example 1.
Figure 5:
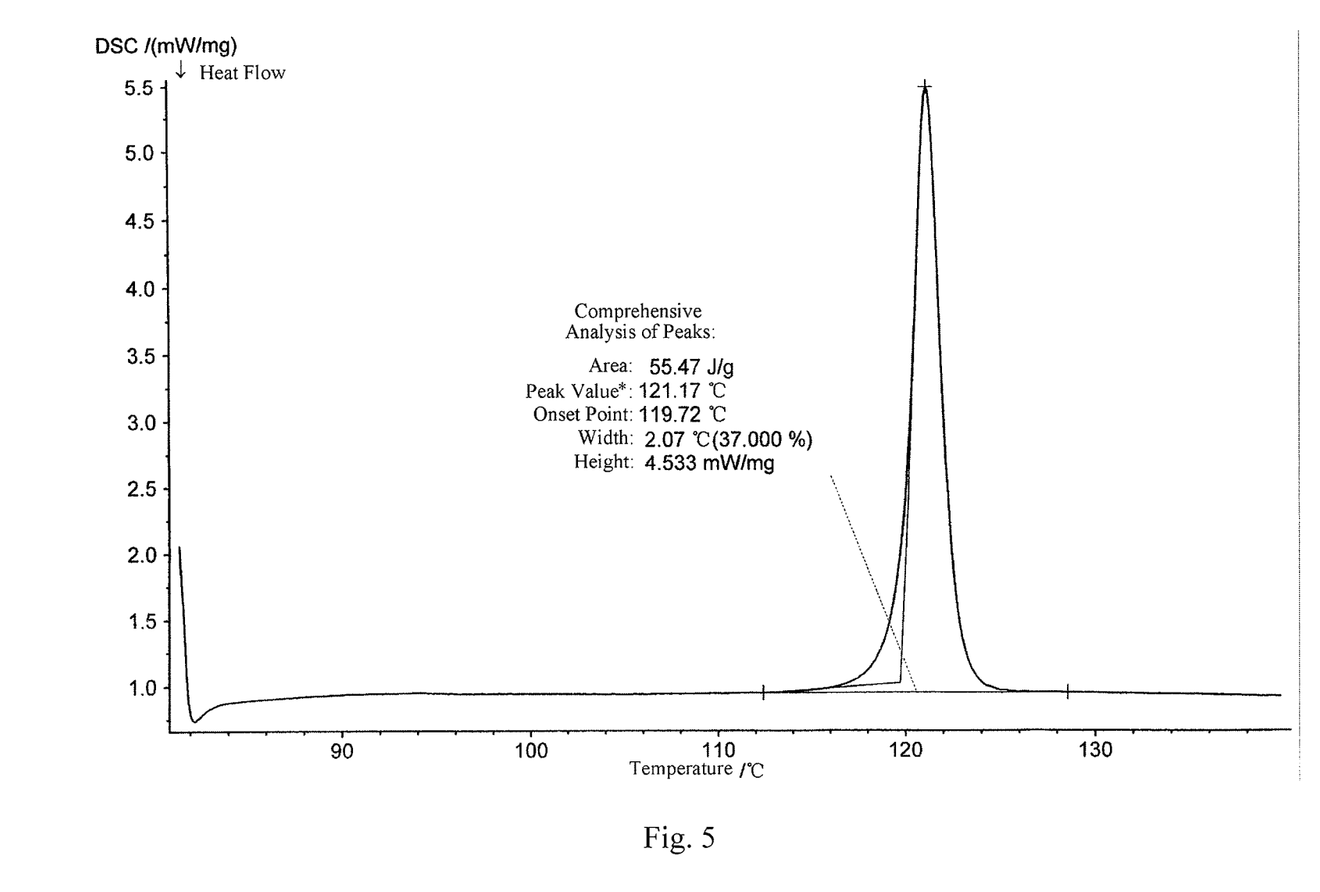
FIG. 5 shows DSC thermogram of crystalline form A of tenofovir dipivoxil fumarate in Comparative Example 1.
Figure 6:
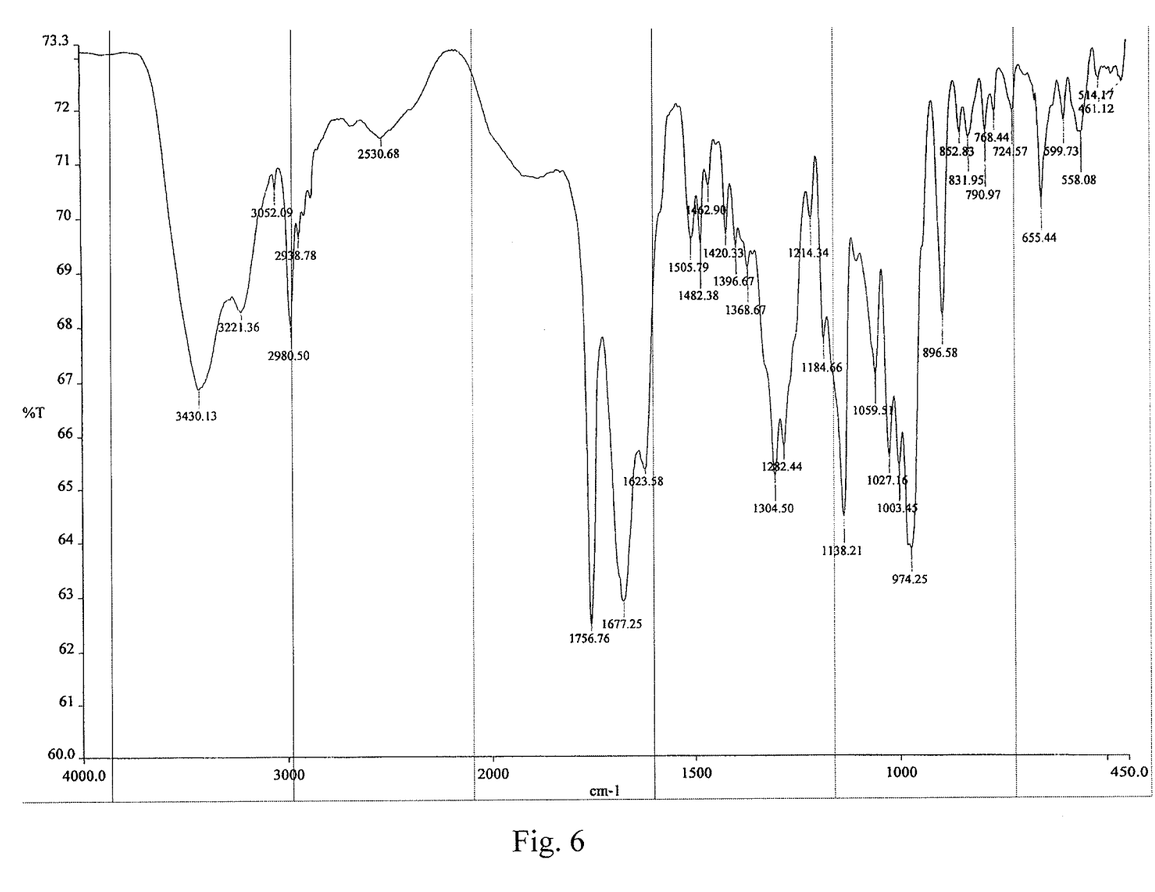
FIG. 6 shows IR spectrum of crystalline form A of tenofovir dipivoxil fumarate in Comparative Example 1.

The XRD pattern, DSC thermogram and IR spectrum of the obtained crystalline form A are shown in FIG. 4, FIG. 5 and FIG. 6, respectively.

COMPARATIVE EXAMPLE 2

Preparation of Tablets of Crystalline Form A of Tenofovir Dipivoxil Fumarate

1. Prescription

| Names of active ingredients and excipients | For 1000 tablets (g) |
|---|---|
| Crystalline form A obtained in Comparative Example 1 | 40 (by weight of tenofovir dipivoxil) |
| Lactose | 50 |
| Pregelatinized starch | 30 |
| Croscarmellose sodium | 3 |
| Magnesium stearate | 1 |

2. Process
(1) Pregelatinized starch and croscarmellose sodium were dried at 105° C. for 2 h, and lactose was dried at 80° C. for 2 h.
(2) Crystalline form A of tenofovir dipivoxil fumarate obtained in Comparative Example I was passed through 80 mesh screen. The dried lactose, pregelatinized starch and croscarmellose sodium were passed through 60 mesh screen, respectively. The screened active ingredients and excipients were mixed together, and then were passed through 60 mesh screen again. After mixed homogeneously, the resulting mixture was dry-granulated. The obtained granules were passed through 20 mesh screen. Magnesium stearate was added and mixed homogeneously.
(3) The resulting mixture was compressed into tablets.

EXAMPLE 1

Preparation of Crystalline Form B of Tenofovir Dipivoxil Fumarate

To 4 kg of ethanol was added 1 kg of tenofovir dipivoxil fumarate. The resulting mixture was heated to 50° C. and stirred. After tenofovir dipivoxil fumarate was dissolved, 8 kg of pure water was added. The mixture was stirred and cooled to 5° C., stood for crystallization for 4 h, and then filtered and dried under reduced pressure at 60° C. to give 0.8 kg of crystalline form B of tenofovir dipivoxil fumarate.

The XRD pattern, DSC thermogram, and IR spectrum of the obtained crystalline form B are shown in FIG. 1, FIG. 2 and FIG. 3, respectively.

EXAMPLE 2

Preparation of Crystalline Form B of Tenofovir Dipivoxil Fumarate

To 3 kg of methanol was added 1 kg of tenofovir dipivoxil fumarate. The resulting mixture was heated to 40° C. and stirred. After tenofovir dipivoxil fumarate was dissolved, 6 kg of pure water was added under stirring, cooled to 0° C., stood for crystallization for 4 h, and then filtered and dried under reduced pressure at 60° C. to give 0.9 kg of crystalline form B of tenofovir dipivoxil fumarate.

EXAMPLE 3

Hard Light Exposure Test of Crystalline Form B of Tenofovir Dipivoxil Fumarate

Crystalline form B obtained in Example 1 was evenly spread out and placed in open culture dishes. The thickness was less than or equal to 5 mm. The culture dishes were placed in an illuminating incubator for 10 days, with the illumination intensity of 4500±500 Lx. The samples were taken on the fifth and tenth day, respectively, for determination of the important test items associated with stability, compared with the results of 0 day. The results are shown in Table 1.

TABLE 1

Hard Light Exposure Test of Crystalline Form B of Tenofovir Dipivoxil Fumarate

| Test conditions | Test items | | 0 (day) | 5 (day) | 10 (day) |
|---|---|---|---|---|---|
| Light exposure | Appearance | | White crystalline powder | White crystalline powder | White crystalline powder |
| | Melting point (° C.) | | 117.2-118.7 | 117.0-118.7 | 117.2-118.7 |
| | Specific optical rotation (°) | | −11.8 | −11.6 | −11.6 |
| | Related substances (%) | Mono ester (%) | 0.20 | 0.18 | 0.19 |
| | | Total amount of other impurities (%) | 0.21 | 0.18 | 0.19 |
| | Content (%) | | 100.0 | 100.1 | 99.7 |

EXAMPLE 4

High Temperature Test of Crystalline Form B of Tenofovir Dipivoxil Fumarate

Two samples of crystalline form B of tenofovir dipivoxil fumarate obtained in Example 1 were evenly spread out and placed in open culture dishes. The thickness was less than or equal to 5 mm. The two samples were placed in 40° C. and 60° C. thermostatic drying chamber for 10 days, respectively. The samples were taken on the fifth and tenth day, respectively, for determination of the important test items associated with stability, compared with the results of 0 day. The results are shown in Table 2 and Table 3.

TABLE 2

High Temperature Test of Crystalline Form B of Tenofovir Dipivoxil Fumarate (40° C.)

| Test conditions | Test items | | 0 (day) | 5 (day) | 10 (day) |
|---|---|---|---|---|---|
| 40° C. | Appearance | | White crystalline powder | White crystalline powder | White crystalline powder |
| | Melting point (° C.) | | 117.2-118.7 | 117.2-118.8 | 117.1-118.7 |
| | Specific optical rotation (°) | | −11.8 | −11.4 | −11.6 |
| | Related substances (%) | Mono ester (%) | 0.20 | 0.23 | 0.24 |
| | | Total amount of other impurities (%) | 0.21 | 0.20 | 0.19 |
| | Content (%) | | 100.0 | 99.9 | 99.8 |

TABLE 3

High Temperature Test of Crystalline Form
B of Tenofovir Dipivoxil Fumarate (60° C.)

| Test conditions | Test items | | 0 (day) | 5 (day) | 10 (day) |
|---|---|---|---|---|---|
| 60° C. | Appearance | | White crystalline powder | White crystalline powder | White crystalline powder |
| | Melting point (° C.) | | 117.2-118.7 | 117.0-118.5 | 117.1-118.5 |
| | Specific optical rotation (°) | | −11.8 | −11.7 | −11.4 |
| | Related substances (%) | Mono ester (%) | 0.20 | 0.28 | 0.33 |
| | | Total amount of other impurities (%) | 0.21 | 0.19 | 0.19 |
| | Content (%) | | 100.0 | 100.1 | 99.9 |

TABLE 4

High Humidity (92.5%) Test of Crystalline
Form B of Tenofovir Dipivoxil Fumarate

| Test conditions | Test items | | 0 (day) | 5 (day) | 10 (day) |
|---|---|---|---|---|---|
| High humidity | Appearance | | White crystalline powder | White crystalline powder | White crystalline powder |
| | Melting point (° C.) | | 117.2-118.7 | 117.1-118.5 | 117.2-118.6 |
| | Specific optical rotation (°) | | −11.8 | −11.5 | −11.8 |
| | Related substances (%) | Mono ester (%) | 0.20 | 0.29 | 0.35 |
| | | Total amount of other impurities (%) | 0.21 | 0.19 | 0.19 |
| | Content (%) | | 100.0 | 99.7 | 100.0 |

EXAMPLE 5

High Humidity Test of Crystalline Form B of Tenofovir Dipivoxil Fumarate

Crystalline form B of tenofovir dipivoxil fumarate obtained in Example 1 was evenly spread out and placed in an open culture dish. The thickness was less than or equal to 5mm. The culture dish was placed in a constant temperature and humidity chamber at 25° C. with relative humidity of 90%±5% for 10 days. The samples were taken on the fifth and tenth day, respectively, for determination of the important test items associated with stability, compared with the results of 0 day. The results are shown in Table 4.

EXAMPLE 6

Acceleration Test of Crystalline Form B of Tenofovir Dipivoxil Fumarate

Crystalline form B of tenofovir dipivoxil fumarate obtained in Example 1 was sealed with a pharmaceutical polyethylene plastic film bag, and placed in a constant temperature and humidity chamber at 40±2° C. with relative humidity of 75% ±5% for 6 months. The samples were taken at the end of the first, second, third, sixth month, respectively, for determination of the important test items associated with stability, compared with the results of 0 month. The results are shown in Table 5.

TABLE 5

Acceleration Test of Crystalline Form B of Tenofovir
Dipivoxil Fumarate (40 ± 2° C.)

| Times (month) | Appearance | Melting point (° C.) | Specific optical rotation (°) | Related substances | | Content (%) |
|---|---|---|---|---|---|---|
| | | | | Monoester (%) | Total amount of other impurities (%) | |
| 0 | White crystalline powder | 117.2-118.7 | −11.8 | 0.20 | 0.21 | 100.0 |
| 1 | White crystalline powder | 117.0-118.2 | −11.5 | 0.29 | 0.22 | 100.0 |
| 2 | White crystalline powder | 117.2-118.5 | −11.6 | 0.35 | 0.23 | 99.9 |
| 3 | White crystalline powder | 117.1-118.8 | −11.5 | 0.42 | 0.25 | 99.8 |
| 6 | White crystalline powder | 117.1-118.4 | −11.5 | 0.47 | 0.26 | 99.4 |

EXAMPLE 7

Preparation of Tablets of Crystalline Form B of Tenofovir Dipivoxil Fumarate 1. Prescription

| Names of active ingredients and excipients | For 1000 tablets (g) |
|---|---|
| Crystalline form B obtained in Example 2 | 40 (by weight of tenofovir dipivoxil) |
| Lactose | 50 |
| Pregelatinized starch | 30 |
| Croscarmellose sodium | 3 |
| Magnesium stearate | 1 |

2. Process (1) Pregelatinized starch and croscarmellose sodium were dried at 105° C. for 2 h and lactose was dried at 80° C. for 2 h.

(2) Crystalline form B of tenofovir dipivoxil fumarate obtained in Example 2 was passed through 80 mesh screen. The dried lactose, pregelatinized starch and croscarmellose sodium were passed through 60 mesh screen, respectively. The screened active ingredients and excipients were mixed together. The resulting mixture was passed through 60 mesh screen again. After mixed homogeneously, the mixture was dry-granulated. The obtained granules were passed through 20 mesh screen. Magnesium stearate was added and mixed homogeneously.

(3) The resulting mixture was compressed into tablets.

EXAMPLE 8

Long-Term Test of Crystalline Form B of Tenofovir Dipivoxil Fumarate

According to the long-term test method described in appendix XIXC of the People's Republic of China Pharmacopeia (2010 Edition), crystalline form B of tenofovir dipivoxil fumarate obtained in Example 1 was sealed with a pharmaceutical polyethylene plastic film bag, and placed under the temperature of 25±2° C. and relative humidity of 60% ±10%. The samples were taken at the end of the third, sixth, ninth and twelfth month, respectively, for determination of the important test items associated with stability, compared with the results of 0 month. The results are shown in Table 6.

TABLE 6

Long-Term Test of Crystalline Form B of Tenofovir Dipivoxil Fumarate
(25 ± 2° C., relative humidity 60% ± 10%)

| Times (month) | Appearance | Melting point (° C.) | Specific optical rotation (°) | Related substances ||||| Content (%) |
|---|---|---|---|---|---|---|---|---|
| | | | | Monoester (%) | R-PMPA (%) | Total amount of other impurities (%) | S-isomer (%) | |
| 0 | White crystalline powder | 117.2-118.7 | −11.8 | 0.20 | undetected | 0.21 | undetected | 100.0 |
| 3 | White crystalline powder | 117.1-118.4 | −11.5 | 0.24 | undetected | 0.22 | undetected | 100.0 |
| 6 | White crystalline powder | 117.1-118.4 | −11.6 | 0.26 | undetected | 0.25 | undetected | 99.9 |
| 9 | White crystalline powder | 117.2-118.4 | −11.5 | 0.30 | undetected | 0.24 | undetected | 100.0 |
| 12 | White crystalline powder | 117.2-118.7 | −11.5 | 0.33 | undetected | 0.19 | undetected | 99.9 |

All patents, patent application publications, patent applications and non-patent publications cited in the specification are incorporated herein in their entireties by reference.

Although the present invention has been described with respect to the specific embodiments for illustration purpose, it should be understood by those skilled in the art according to the above content that various modifications may be made without departing from the true spirit and scope of the invention. Accordingly, the scope of the present invention should only be defined by the claims appended hereto.

What is claimed is:

1. A crystalline form of tenofovir dipivoxil fumarate, having an X-ray powder diffraction pattern using Cu-Kα radiation, expressed in terms of lattice spacing "d" comprising peaks at 18.4714Å, 5.0350Å, 4.6380Å, 4.5347Å, 4.3838Å, 4.2874Å and 3.6304 Å.

2. The crystalline form of claim 1, having an X-ray powder diffraction pattern using Cu-Kα radiation, expressed in terms of lattice spacing "d" comprising peaks at 18.4714Å, 8.3234Å, 6.0870Å, 5.0350Å, 4.7262Å, 4.6380Å, 4.5347Å, 4.3838Å, 4.2874Å, 3.9414Å and 3.6304 Å.

3. The crystalline form of claim 2, having an X-ray powder diffraction pattern using Cu-Kα radiation, expressed in terms of lattice spacing "d" comprising peaks at 18.4714Å, 8.3234Å, 6.7220Å, 6.4396Å, 6.0870Å, 5.0350Å, 4.7262Å, 4.6380Å, 4.5347Å, 4.3838Å, 4.2874Å, 3.9414Å and 3.6304 Å.

4. The crystalline form of claim 3, having an X-ray powder diffraction pattern using Cu-Kα radiation, expressed in terms of lattice spacing "d" comprising peaks at 18.4714Å, 8.7854Å, 8.3234Å, 6.7220Å, 6.4396Å, 6.0870Å, 5.7268Å, 5.3106Å, 5.0350Å, 4.8756Å, 4.7262Å, 4.6380Å, 4.5347Å, 4.3838Å, 4.2874Å, 4.0772Å, 3.9414Å, 3.6304Å, 3.5561Å, 3.0194Å and 2.9800Å.

5. A crystalline composition comprising the crystalline form of claim 1, wherein the crystalline form is more than 50% by weight of the composition.

6. A process for preparing the crystalline form of claim 1, comprising
   (a) dissolving tenofovir dipivoxil fumarate in an organic solvent by heating, wherein the organic solvent is a lower alcohol or a lower ketone;
   (b) adding water; and
   (c) precipitating a crystalline form of tenofovir dipivoxil fumarate.

7. The process of claim 6, wherein the step (c) is carried out under cooling.

8. The process of claim 6, further comprising
   (d) filtrating; and
   (e) drying.

9. The process of claim 6, comprising
   (a) dissolving tenofovir dipivoxil fumarate in an organic solvent by heating, wherein 2 Kg to 6 Kg of the organic solvent is used per kilogram of tenofovir dipivoxil fumarate, the organic solvent is selected from one or more solvents of methanol, ethanol, propanol, isopropanol, n-butanol, isobutanol, tert-butanol, acetone and butanone, and the heating temperature is 35° C. to 70° C.;
   (b) adding water, wherein 5 Kg to 15 Kg of water is added per kilogram of tenofovir dipivoxil fumarate; and
   (c) precipitating a crystalline form of tenofovir dipivoxil fumarate.

10. The process of claim 9, wherein the step (c) is carried out with cooling to a temperature of −10° C. to 5° C.

11. The process of claim 9, further comprising
    (d) filtrating; and
    (e) drying under reduced pressure at a temperature range of 40° C. to 70° C.

12. A pharmaceutical composition, comprising a therapeutically effective amount of the crystalline form of claim 1.

13. A method for ameliorating HIV and HBV infection in a mammal, comprising administrating a therapeutically effective amount of the crystalline form of claim 1 to the mammal in need thereof.

14. A crystalline composition comprising the crystalline form of claim 2, wherein the crystalline form is more than 50% by weight of the composition.

15. A crystalline composition comprising the crystalline form of claim 3, wherein the crystalline form is more than 50% by weight of the composition.

16. A crystalline composition comprising the crystalline form of claim 4, wherein the crystalline form is more than 50% by weight of the composition.

17. A method for relieving symptoms caused by HIV and HBV infection in a mammal, comprising administrating a therapeutically effective amount of the crystalline form of claim 1 to the mammal in need thereof.

\* \* \* \* \*